(12) United States Patent
Sheng et al.

(10) Patent No.: US 11,312,075 B2
(45) Date of Patent: Apr. 26, 2022

(54) OPTICAL ENGINE FOR THREE-DIMENSIONAL PRINTING

(71) Applicant: Texas Instruments Incorporated, Dallas, TX (US)

(72) Inventors: Zhongyan Sheng, Allen, TX (US); Stephen Aldridge Shaw, Plano, TX (US); Steven Edward Smith, Allen, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 76 days.

(21) Appl. No.: 16/660,542

(22) Filed: Oct. 22, 2019

(65) Prior Publication Data
US 2020/0122394 A1  Apr. 23, 2020

Related U.S. Application Data

(60) Provisional application No. 62/749,251, filed on Oct. 23, 2018.

(51) Int. Cl.
*B29C 64/277* (2017.01)
*B33Y 10/00* (2015.01)
*B29C 64/129* (2017.01)
*B33Y 30/00* (2015.01)
*H04W 4/80* (2018.01)
(Continued)

(52) U.S. Cl.
CPC ............ *B29C 64/277* (2017.08); *A61B 5/038* (2013.01); *A61B 5/746* (2013.01); *A61J 17/103* (2020.05); *A61J 17/1011* (2020.05); *A61J 17/1012* (2020.05); *B29C 64/129* (2017.08); *B33Y 10/00* (2014.12); *B33Y 30/00* (2014.12);
(Continued)

(58) Field of Classification Search
CPC ............... G02B 26/08; G02B 26/0808; G02B 26/0816; G02B 26/0825; G02B 26/0833; G02B 26/0841; G02B 26/085; G02B 26/0858; G02B 26/0866; G02B 26/0785; G02B 26/0883; G02B 26/0891; B29C 64/277; B29C 64/282
See application file for complete search history.

(56) References Cited

U.S. PATENT DOCUMENTS 5,504,514 A * 4/1996 Nelson ................. B41J 2/465
347/130
2004/0141742 A1 * 7/2004 So ...................... G02B 26/0841
398/45

(Continued)

*Primary Examiner* — Joseph S Del Sole
*Assistant Examiner* — Jamel M Nelson
(74) *Attorney, Agent, or Firm* — Michelle F. Murray; Charles A. Brill; Frank D. Cimino

(57) ABSTRACT

A spatial light modulator outputs modulated light including: modulated first light when the spatial light modulator receives first light; and modulated second light when the spatial light modulator receives second light. Projection optics project the modulated light onto: a first pixel region when a component or the spatial light modulator has a first position; and a second pixel region when the component or the spatial light modulator has a second position. The first and second pixel regions partially overlap. A pixel shifter moves the component or the spatial light modulator between: the first position when the spatial light modulator outputs the modulated first light; and the second position when the spatial light modulator outputs the modulated second light.

26 Claims, 17 Drawing Sheets

(51) Int. Cl.
    *A61J 17/00*  (2006.01)
    *A61B 5/03*  (2006.01)
    *A61B 5/00*  (2006.01)
    *G02B 3/00*  (2006.01)
    *G02B 26/08*  (2006.01)

(52) U.S. Cl.
    CPC ............ *H04W 4/80* (2018.02); *A61J 2200/72* (2013.01); *G02B 3/0037* (2013.01); *G02B 26/0833* (2013.01)

(56) References Cited

U.S. PATENT DOCUMENTS

| | | | |
|---|---|---|---|
| 2005/0083565 A1* | 4/2005 | Yamazaki | H04N 9/315 359/244 |
| 2017/0072635 A1* | 3/2017 | El-Siblani | B29C 64/357 |

\* cited by examiner

OPTICAL ENGINE FOR THREE-DIMENSIONAL PRINTING

CROSS-REFERENCE TO RELATED APPLICATION

This application claims the benefit under 35 U.S.C. § 119(e) to co-owned U.S. Provisional Patent Application Ser. No. 62/749,251, filed Oct. 23, 2018, entitled "ENHANCED 3D PRINTING USING PIXEL LEVEL SCAN," which is hereby incorporated herein by reference in its entirety.

TECHNICAL FIELD

This relates generally to three-dimensional printing, and in examples, to stereolithographic apparatus (SLAs).

BACKGROUND

Three-dimensional printing is useful in many fields, such as manufacturing and artistic design. The cost of three-dimensional printing is falling; thus, making more and more applications for this technology financially feasible. One type of three-dimensional printer is the photo-polymerization printer or stereolithographic apparatus (SLA). This type of printer uses light to convert a liquid polymer to a solid. One type of photo-polymerization printer is a vat type. This type of printer uses a vat with a transparent bottom to contain photo-polymerizable liquid. Initially, a lift plate is one layer from the bottom of the vat. Each printer has a layer thickness that the printer develops, which may be tens to hundreds of microns thick. An optical engine is below the vat. The optical engine uses light to expose a pattern for the initial layer derived from a three-dimensional electronic model of the object to be printed. The light causes the liquid in the vat to polymerize in that pattern and thus form solid material. The lift plate then rises a layer and then exposes the next layer of the object. This process repeats until the printer forms all layers of the object.

With photo-polymerization printers, the optical engine can produce layers with high resolution. For example, a digital light processing (DLP) optical engine can produces patterns with millions of pixels. However, the optical resolution of the spatial light modulator limits resolution of the printed device.

SUMMARY

A spatial light modulator outputs modulated light including: modulated first light when the spatial light modulator receives first light; and modulated second light when the spatial light modulator receives second light. Projection optics project the modulated light onto: a first pixel region when a component or the spatial light modulator has a first position; and a second pixel region when the component or the spatial light modulator has a second position. The first and second pixel regions partially overlap. A pixel shifter moves the component or the spatial light modulator between: the first position when the spatial light modulator outputs the modulated first light; and the second position when the spatial light modulator outputs the modulated second light.

DETAILED DESCRIPTION

Figure 1:
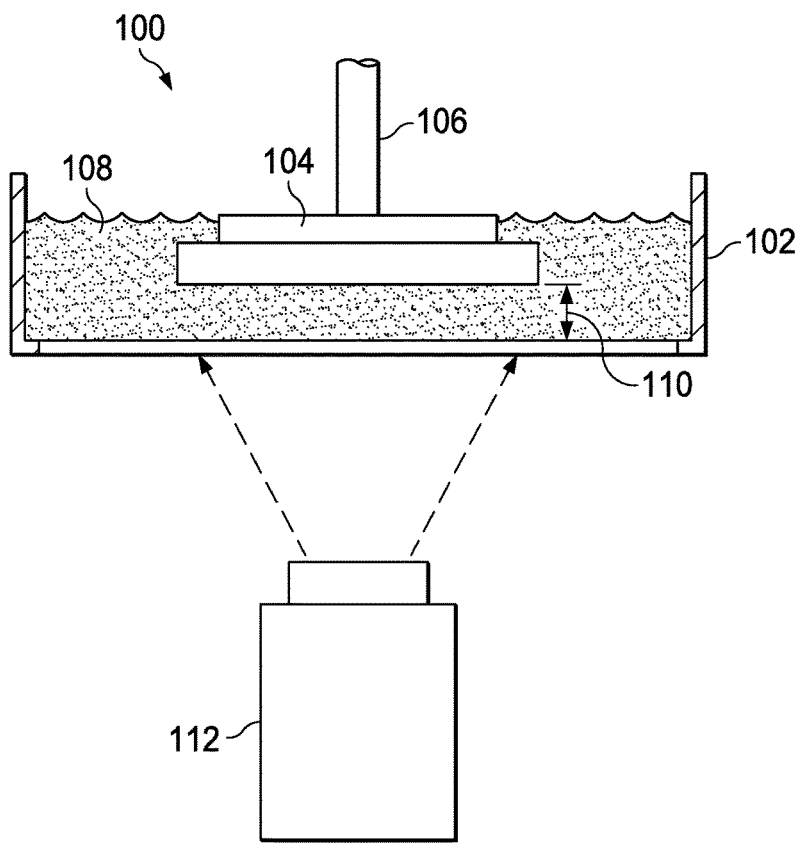
FIG. 1 is a diagram of a three-dimensional printer.

In the drawings, corresponding numerals and symbols generally refer to corresponding parts unless otherwise indicated. The drawings are not necessarily drawn to scale.

In this description, the term "coupled" may include connections made with intervening elements, and additional elements and various connections may exist between any elements that are "coupled." Elements are referred to herein as "optically coupled" when a connection between the elements involves transmission or reception of light.

In example arrangements, the problem of providing finer resolution in three-dimensional printing is solved by using illumination below a curing threshold and overlapping at least two pixels so that the combined illumination in the overlapped area is above the curing threshold. In an example, a spatial light modulator outputs modulated light including: modulated first light when the spatial light modulator receives first light; and modulated second light when the spatial light modulator receives second light. Projection optics project the modulated light onto: a first pixel region when a component or the spatial light modulator has a first position; and a second pixel region when the component or the spatial light modulator has a second position. The first and second pixel regions partially overlap. A pixel shifter moves the component or the spatial light modulator between: the first position when the spatial light modulator outputs the modulated first light; and the second position when the spatial light modulator outputs the modulated second light.

FIG. 1 is a diagram of a three-dimensional printer 100. Three-dimensional printer 100 prints a three-dimensional object layer-by-layer from an electronic model of the object. Vat 102 has a transparent bottom. Control arm 106 positions lift plate 104 in vat 102. Photo-polymerizing resin 108 fills vat 102. Control arm 106 positions lift plate 104 at a layer thickness 110 from the bottom of vat 102. In examples, the layer thickness is 0.05 to 0.15 mm. When the lift plate is in position, optical engine 112 projects light in a pattern of the first layer of the object to be printed. Where light from the optical engine 112 strikes photo-polymerizing resin 108, photo-polymerizing resin polymerizes and forms solid material. Thus, the first layer of the object to be printed is formed.

The first layer adheres to lift plate 104. Control arm 106 then lifts lift plate 104 by another layer thickness 110. In some examples, control arm 106 lifts, twists and/or tilts lift plate 104 to release the first layer from the bottom of vat 102. When the lift plate 104 is in position for the next layer of the object, optical engine 112 projects light in the pattern of the next layer of the object. Three-dimensional printer 100 repeats this process until all layers of the object are printed.

Figure 2:
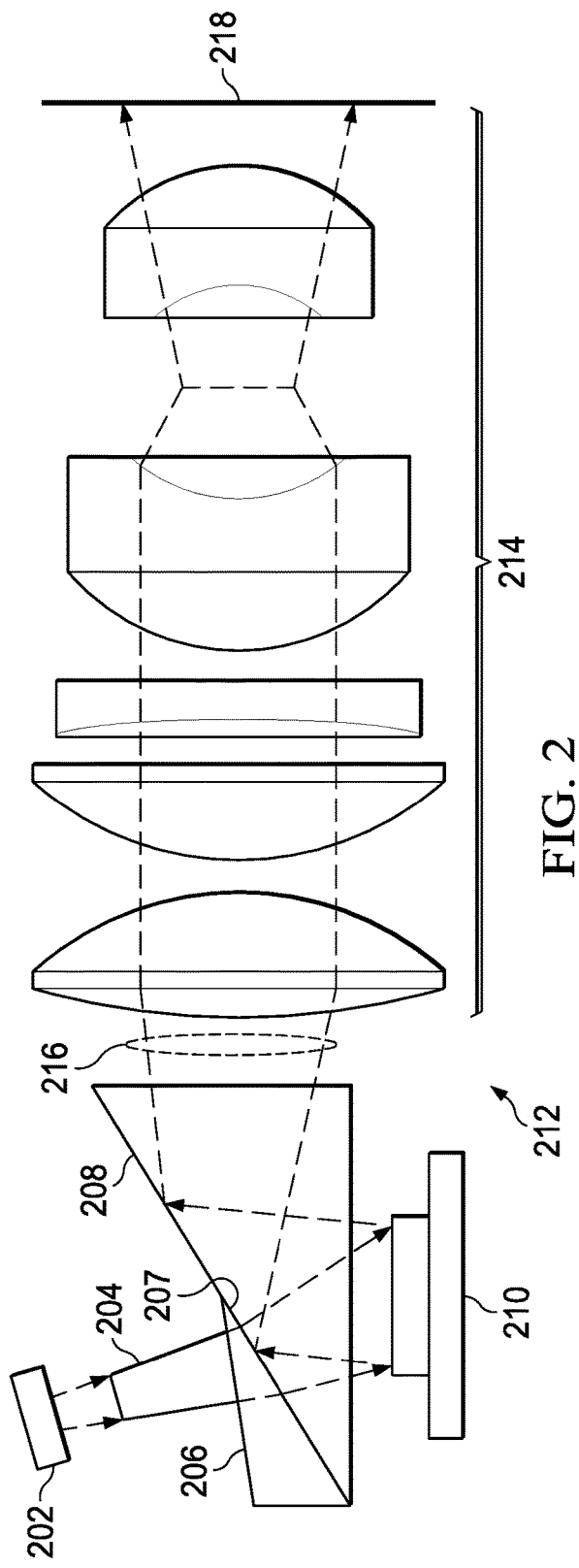
FIG. 2 is a diagram of an example optical engine.

FIG. 2 is a diagram of an example optical engine 212. Optical engine 212 is like optical engine 112 (FIG. 1). Light source 202 is a light emitting diode (LED) in this example. In other examples, light source 202 is another source of light, such as laser diode or a high intensity incandescent light. In this example, the LED produces 1255 mW of optical power. The wavelength of light produced by light source 202 is selected for efficient polymerization of photo-polymerizing resin 108 (FIG. 1). In this example, light source 202 produces light of approximately 405 nm. In other examples, light source 202 produces light in a range of 350-460 nm. In many light sources for optical engines, light from the light source is collimated at the output of the light source. However, this requires additional lenses at the output of light source 202. In this example, the input of light integrator 204 is proximate to light source 202. This captures as much light as possible without the need for collimating lenses. In addition, in this example, the form factor of the input of light integrator 204 is approximately the same as the form factor of the output of light source 202, which increases the portion of light from light source 202 that enters light integrator 204.

The output of light integrator 204 is larger than the input of light integrator 204. This configuration lowers the spread of light from the output of light integrator 204 so that the light is efficiently provided to spatial light modulator 210. Light integrator 204 homogenizes the light from light source 202 by multiple reflections of the light inside light integrator 204. In addition, light integrator 204 helps direct as much light as possible onto spatial light modulator 210. As used herein, the term "light integrator" includes light tunnels, integrating rods, light pipes, and compound parabolic concentrators. Although other types of devices perform light integration, such as micro-lens arrays, these other types of devices are not included in the term "light integrator" as used herein. In this example, light integrator 204 is a light tunnel.

Divergent light from the output of light integrator 204 passes through cover prism 206. The divergent light from the output of light integrator 204 has a form that roughly matches the form factor of spatial light modulator 210. Cover prism 206 provides a surface that is perpendicular to the propagation path of the output of light integrator 204 to lower distortion of the form of light output from light integrator 204. In addition, the higher refractive index of cover prism 206 relative to air lowers the divergence of the light from the output of light integrator 204. The light then passes through an air gap 207 and through reverse total internal reflection prism (RTIR prism) 208. In this example, spatial light modulator 210 is a digital micromirror device (DMD). Other examples use other spatial light modulators, such as liquid crystal on silicon (LCOS) modulators. With DMDs, each pixel is a movable mirror that modulates light by reflecting in an ON direction or an OFF direction, depending on the data for that pixel provided to the DMD. Thus, spatial light modulator 210 addresses multiple pixel positions. The angle of the surface of RTIR prism 208 closest to light integrator 204 is such that it reflects ON direction light from pixels reflecting of spatial light modulator 210 but does not reflect light from light integrator 204. Therefore, the image for projection reflects from RTIR prism 208 to projection optics 214. Projection optics 214 includes components such as at least one lens and/or a pupil. As noted above, the light from light source 202 is not collimated before light integrator 204. The pixels of spatial light modulator 210 are mirrors, therefore modulated divergent output light 216 is also divergent as it enters projection optics 214. Projection optics are often telecentric and thus designed for non-divergent and non-convergent (i.e. collimated) light that has an infinite input focal distance. In this example, modulated divergent output light 216 is divergent, so projection optics 214 must have an input focal point directed to the point of divergence, and thus is non-telecentric. Because light integrator 204 modifies the divergence of the light from light source 202, the point of divergence or input focal point is calculated using the angle of divergence of the light at the output of light integrator 204. The output of projection optics 214 focuses on a target 218. That is, the focal point of projection optics 214 is on the photo-polymerizing resin 108 (FIG. 1) between the lift plate 104 (FIG. 1) and the bottom of vat 102 (FIG. 1). In an example, projection optics 214 may include five lenses using N-BK7 glass. In this example, the five lenses are spherical. In an example, projection optics 204 has an f-number of 3. Co-pending non-provisional patent application (TI-79946) includes further details of the example of FIG. 2.

Figure 3C:
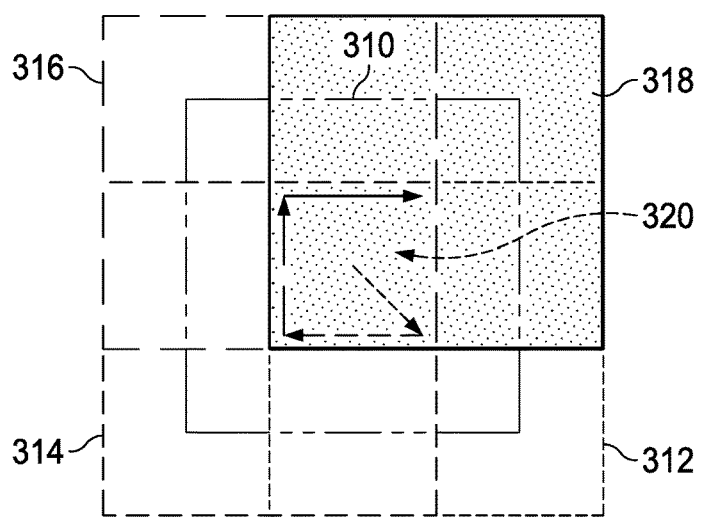
FIGS. 3A-3C (collectively "FIG. 3") are diagrams showing example shifting pixels.
Figure 3B:
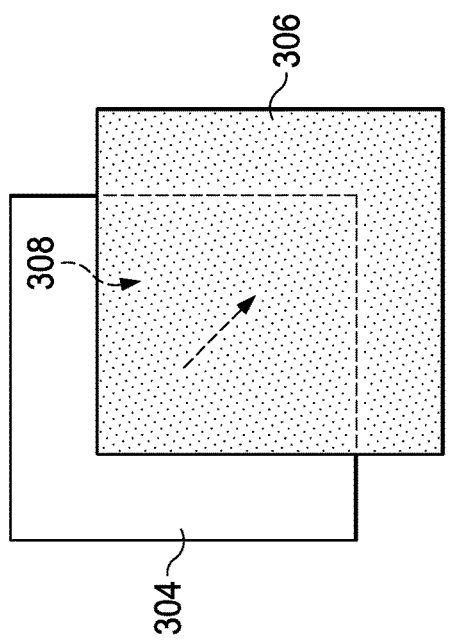
Figure 3A:
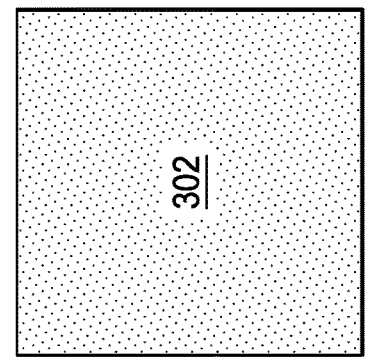

FIGS. 3A-3C (collectively "FIG. 3") are diagrams showing example shifting pixels. As shown in FIG. 3A, pixel 302 is an image or light signal provided by the reflection from one pixel of a spatial light modulator like spatial light modulator 210 (FIG. 2). As shown in FIG. 3B, pixel 304 is another pixel image along with pixel 306. Pixel 306 is a light signal provided by the same pixel of spatial light modulator 210 (FIG. 2) but shifted in both the x and y directions. This leaves an overlap 308 illuminated by both pixel 304 and pixel 306. As is further explained hereinbelow, if total illumination intensity (illumination level multiplied by the illumination time) for pixel 304 and pixel 306 is less that a curing threshold of photo-polymerizing resin 108 (FIG. 1) but the combined total illumination intensity of pixel 304 and 306 is greater than the curing threshold, only overlap 308 is cured, thus curing an area that is smaller (higher resolution) than pixel 304 or pixel 306. In FIG. 3B, pixel 304 and pixel 306 have overlap on 9/16 of the size of pixel 304 and pixel 306. However, this example may use other size overlaps. In addition, the pixel may shift more than once. For example, as shown in FIG. 3C, pixel 310 may provide one fifth of the curing threshold total illumination intensity. This pixel shifts to pixel 312 in both the x and y directions, which also provides one fifth of the curing threshold total illumination intensity. The pixel then shifts in the x direction to pixel 314, which also provides one fifth of the curing threshold total illumination intensity. This pixel then shifts in the y direction to pixel 316, which also provides one fifth of the curing threshold total illumination intensity. This pixel then shifts in the x direction to pixel 318, which also provides one fifth of the curing threshold total illumination intensity. The only portion covered by each of pixel 310, pixel 312, pixel 314, pixel 316 and pixel 318 is area 320.

Therefore, area 320 is the only area that receives a full threshold curing illumination intensity. Thus, this example only cures area 320, which is a much smaller area (higher resolution) than the pixel (pixel 310, pixel 312, pixel 314, pixel 316 and pixel 318) used to illuminate area 320.

Figure 4:
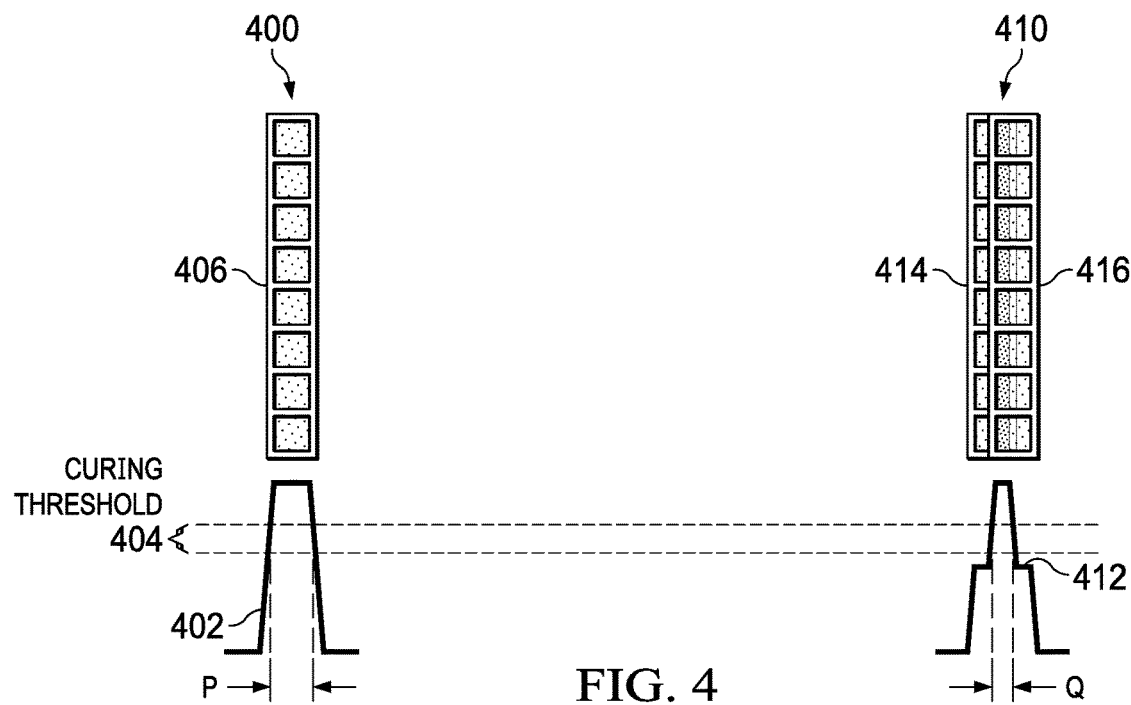
FIG. 4 is a diagram showing two example curing strategies.

FIG. 4 is a diagram showing two example curing strategies. Strategy 400 creates a curing pattern one pixel wide and eight pixels long. Illumination intensity 402 is an intensity above curing threshold 404 across the width of pixels 406. Thus, strategy 400 produces a line of eight pixels long and one pixel wide in the photo-polymerizing resin 108 (FIG. 1). This produces a line one-pixel wide P. On the other hand, strategy 410 applies an illumination intensity 412 that is below curing threshold 404 in a first pixel position 414, and then shifts to a second pixel position 416 and applies the illumination intensity 412 again. Thus, in this example, the first pixel position and the second pixel position receive the same illumination intensity. The area of overlap Q between first pixel position 414 and second pixel position 416 receives twice the illumination intensity 412, which is above the curing threshold 404. Because overlap Q is the only region that receives an illumination intensity above the curing threshold 404, a line eight pixels long and overlap Q wide forms in the photo-polymerizing resin 108 (FIG. 1). Thus, strategy 410 produces a line that has a higher resolution than strategy 400.

Figure 5:
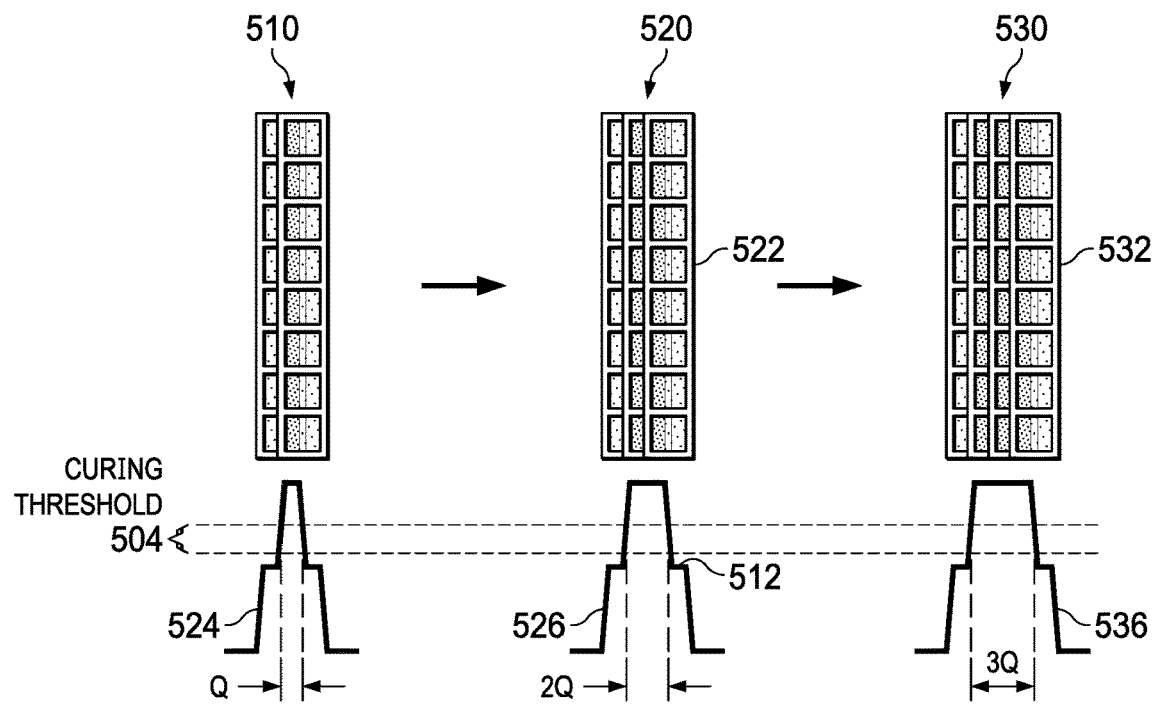
FIG. 5 is a diagram of an example process to extend the cured area of the process of FIG. 4.

FIG. 5 is a diagram of an example process to extend the cured area of the process of FIG. 4. Step 510 is like strategy 410 (FIG. 4). Threshold 504 is like curing threshold 404 (FIG. 4). In step 520, either the original eight pixels shift to the right or adjacent pixels are already in or are shifted to the position of pixels 522. The example then applies illumination level 512 to pixels 522. Illumination profile 524 is like the illumination profile of strategy 410 of FIG. 4. Adding the illumination intensity of pixels 522 creates illumination profile 526, which adds a width Q to the portion of the photo-polymerizing resin 108 (FIG. 1) cured in step 510. Therefore, this example cures a 2 Q wide line, where Q is a width less than the resolution of pixels 522. In step 530 either the original eight pixels shift to the right or adjacent pixels are already in or are shifted to the position of pixels 532. Pixels 532 provide an illumination intensity of 512. This illumination intensity along with the illumination profile 526 produces illumination profile 536, with a cured region of photo-polymerizing resin 108 (FIG. 1) having a width of 3 Q. Thus, the process steps of FIG. 5 can form a feature of any desired width.

Figure 6:
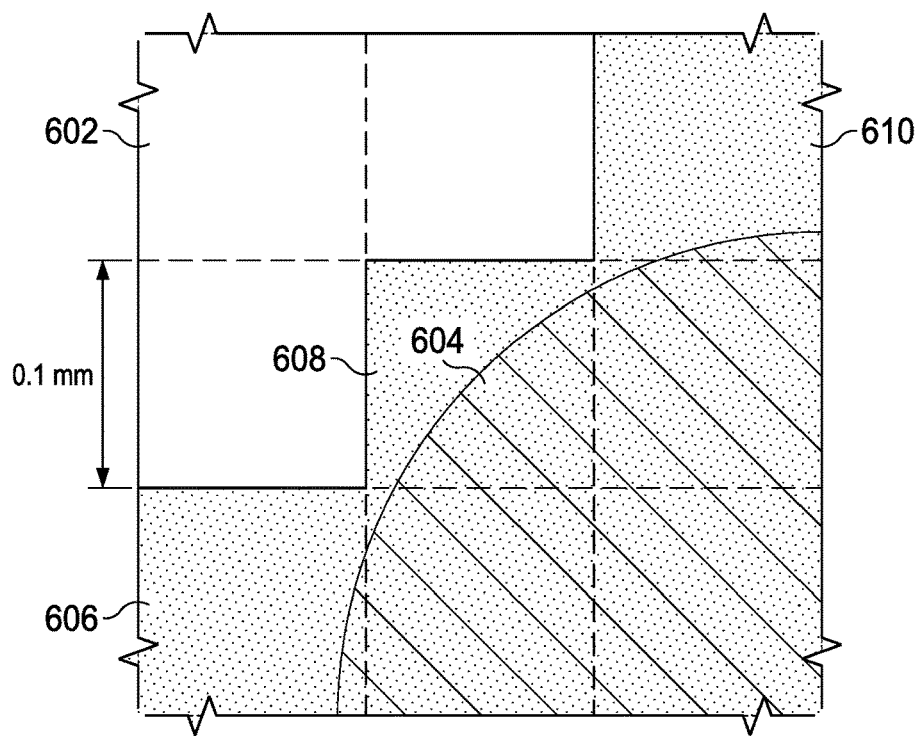
FIG. 6 is a diagram showing an example result of forming a more complex feature with a fixed pixel size.

FIG. 6 is a diagram showing an example result of forming a more complex feature with a fixed pixel size. Pixels 602 are squares that a 0.1 mm on a side. The pattern being cured is quarter circular pattern 604. A shown in FIG. 6, the curvature of pattern 604 does not match well with pixel 606, pixel 608 and pixel 610. Thus, using pixels 602 to produce pattern 604 creates a sawtooth pattern formed by pixels 606, 608 and 610.

Figure 7:
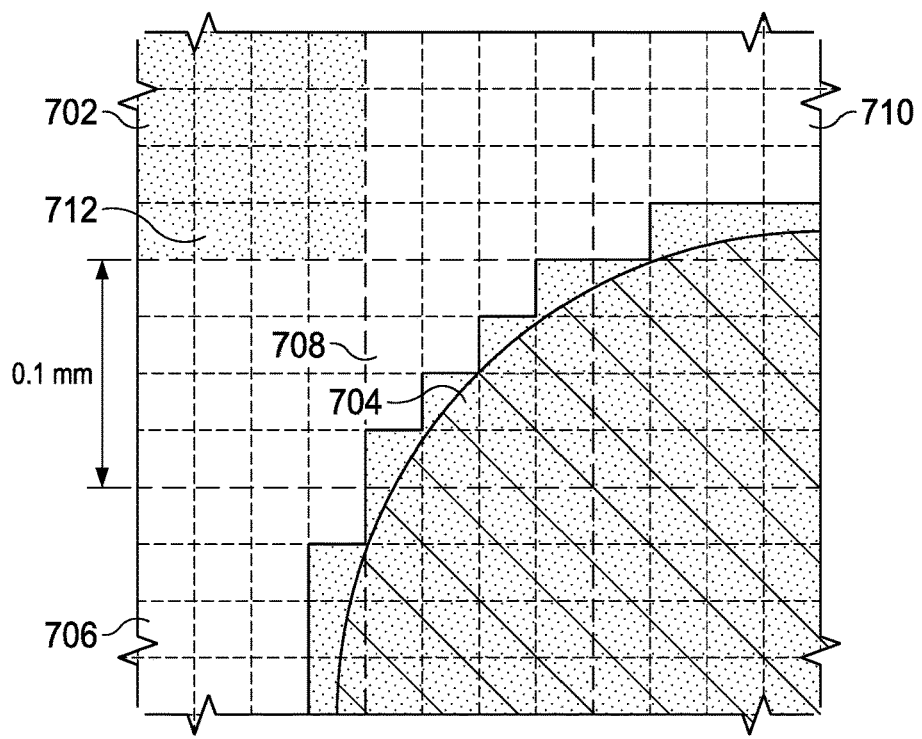
FIG. 7 is a diagram of the result of forming a pattern using an example process.

FIG. 7 is a diagram of the result of forming a pattern 704 using an example process. In this example, pixel shifting and below curing threshold illumination allows for curing of a portion of the pixels like pixel 702. As shown in FIG. 7, each pixel, like pixel 702, includes sixteen addressable subpixels, like subpixel 712. That is, the process shown in FIGS. 3-5 allows for addressing subpixels like subpixel 712 with an above-threshold illumination intensity. Using only those subpixels of pixel 706, pixel 708 and pixel 710 that include pattern 704, produces a much smother and accurate pattern.

Figure 8:
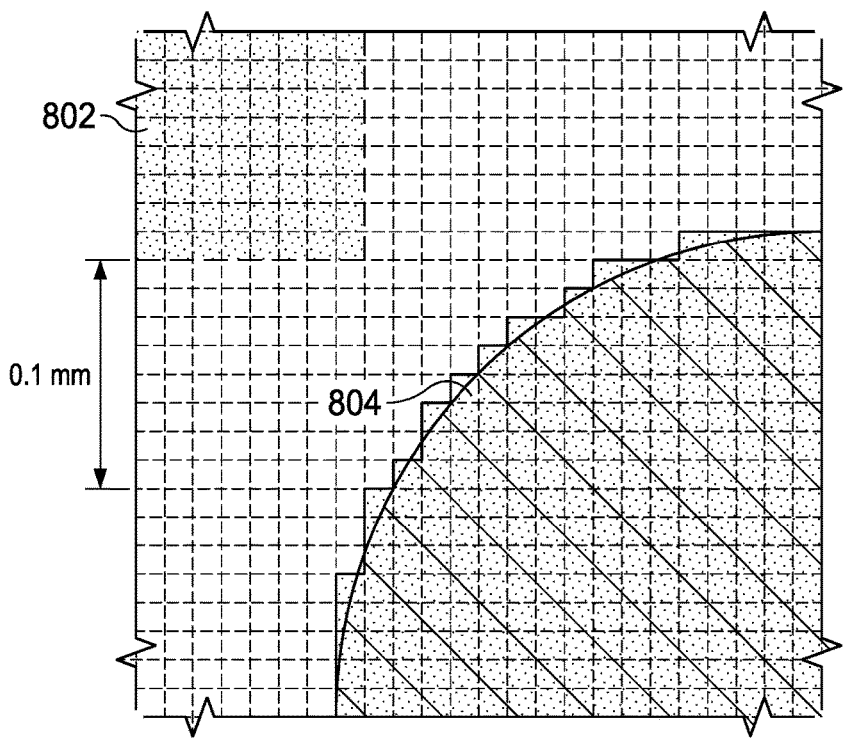
FIG. 8 is a diagram showing an example of the process of FIG. 7 with smaller subpixels.

FIG. 8 is a diagram showing an example of the process of FIG. 7 with smaller subpixels. In the example of FIG. 8, pixel 802 includes sixty-four subpixels as opposed to the sixteen subpixels of pixel 702 (FIG. 7). Thus, the process of FIG. 8 produces an even more accurate depiction of pattern 804. The trade-off is that dividing pixel 802 into sixty-four subpixels requires additional shifting and exposure. Thus, using sixty-four subpixels is slower than sixteen subpixels.

Figure 9A:
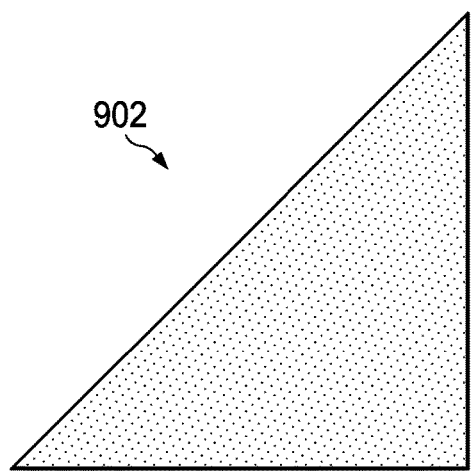
FIGS. 9A-9D (collectively "FIG. 9") are diagrams of an example process using an analog pixel shift.
Figure 9B:
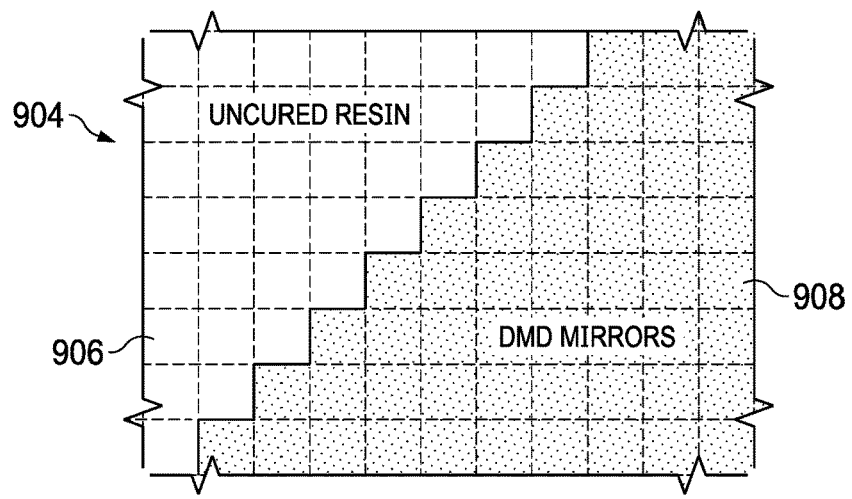
Figure 9C:
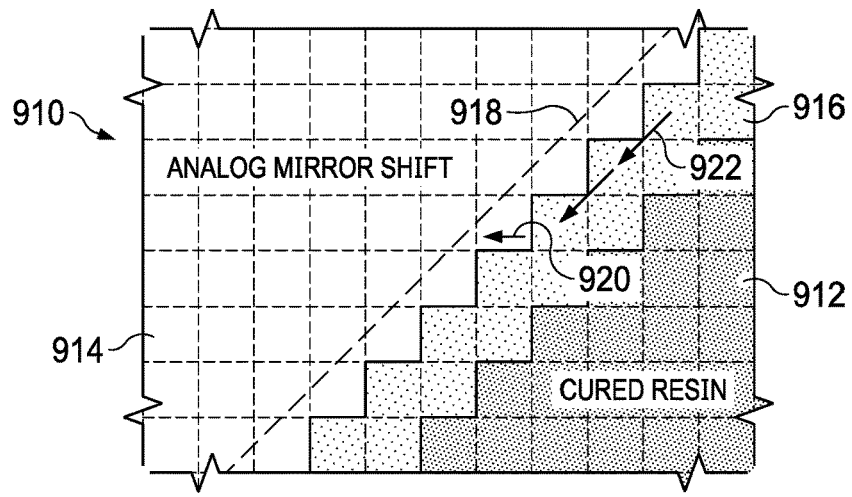
Figure 9D:
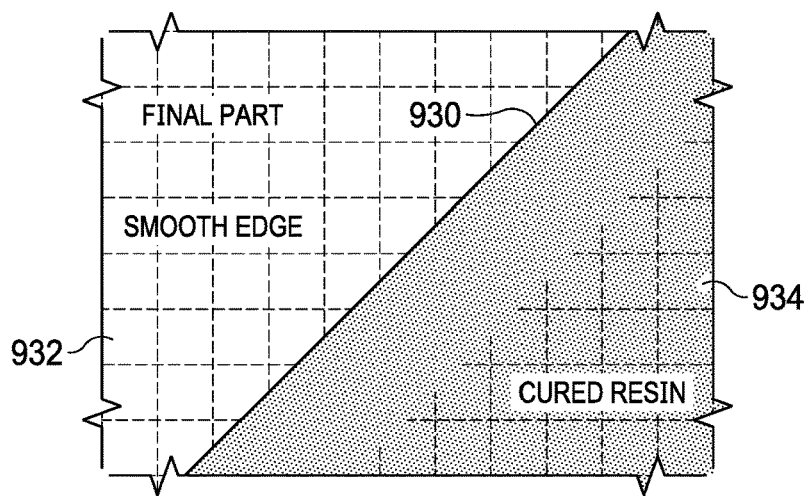

FIGS. 9A-9D (collectively "FIG. 9") are diagrams of an example process using an analog pixel shift. As shown in FIG. 9A, pattern 902 is a triangular pattern for reproduction in the cured resin (like photo-polymerizing resin 108 (FIG. 1)). As shown in FIG. 9B, array 904 shows the layout of pattern 902 onto an array of pixels. Pixels 906 are uncured pixels and pixels 908 are cured pixels. As shown, the edge of pattern 902 is a stair step using this arrangement. As shown in FIG. 9C, array 910 shows an array of pixels in an initial step of an example process. An illumination intensity like illumination level 402 (FIG. 4) cures pixels 912. At this step, pixels 914 are uncured. An illumination level applied to pixels 916 is below the curing threshold. The pixels 916 shift left ("left" being relative to the page) by an amount such that the upper left corners of the top pixels ("top" being relative to the page) align with line 918 as shown by arrow 920. An analog shifting mechanism (further explained hereinbelow) can shift the pixels by any selected distance within the precision level of the shifting mechanism and the driving circuitry. The analog shifting mechanism then moves pixels 916 parallel to line 918 as shown by arrows 922. One example illuminates pixels 916 while shifting. As shown in FIG. 9D, this produces a smooth line 930 between the uncured pixels 932 and the cured pixels 934. Another example shifts pixels 916 by a selected amount before illumination. In this example, the smaller the shift, the smoother line 930 will be. However, reducing the shift increment increases the time necessary to cure the resin to the desired configuration.

Figure 10A:
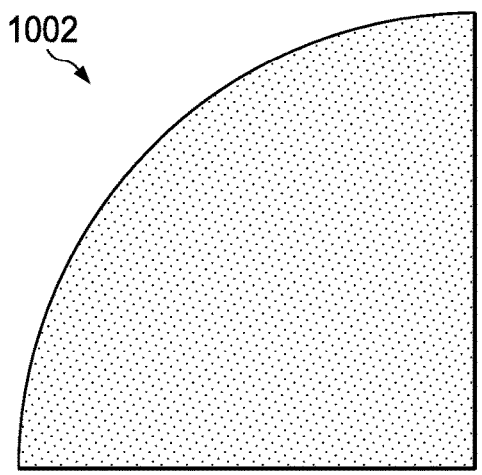
FIGS. 10A-10E (collectively "FIG. 10") are diagrams of another example process using an analog pixel shift.
Figure 10B:
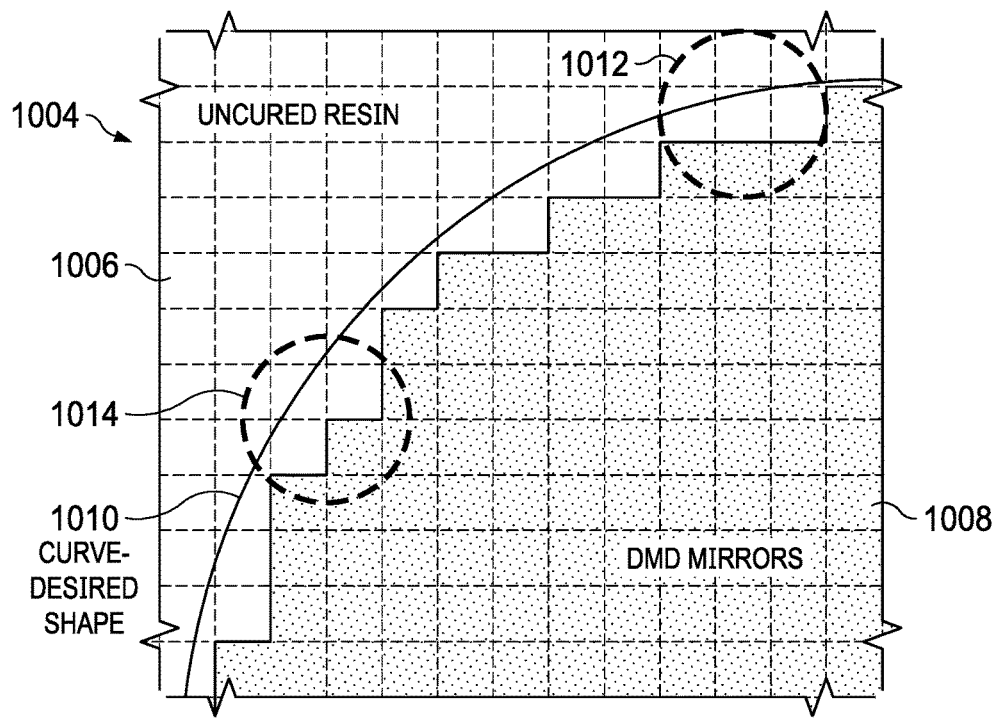
Figure 10C:
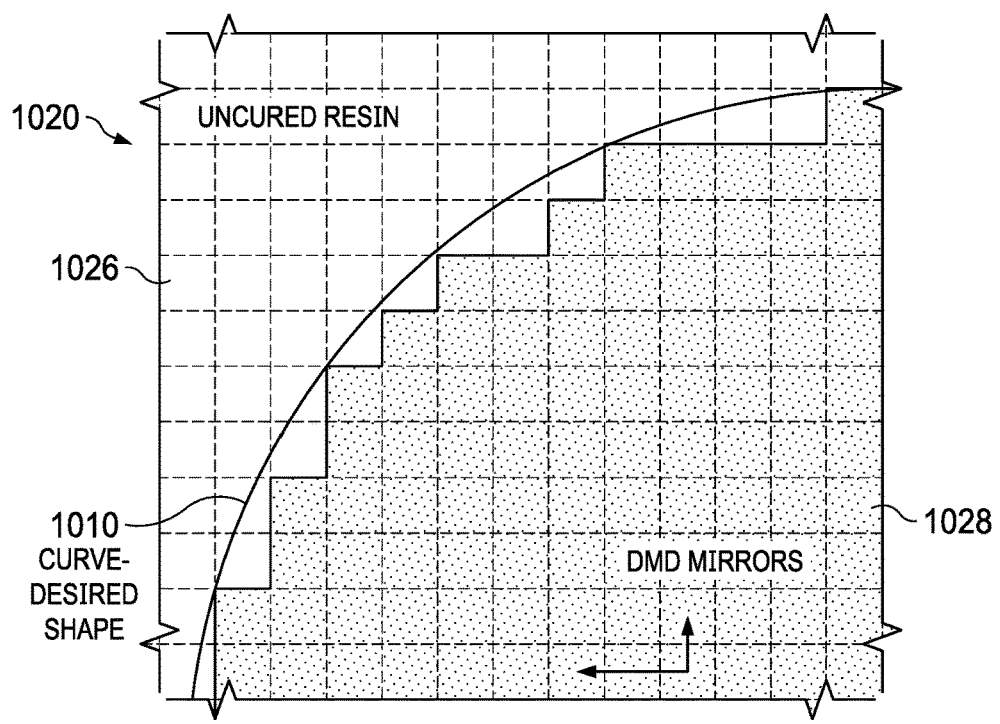

FIGS. 10A-10E (collectively "FIG. 10") are diagrams of another example process using an analog pixel shift. As shown in FIG. 10A, pattern 1002 is a quarter circle pattern for reproduction in the cured resin (like photo-polymerizing resin 108 (FIG. 1)). In other arrangements, the pixel density of the light modulation limits the accuracy of pattern 1002. As shown in FIG. 10B, array 1004 shows the layout of pattern 1002 onto an array of pixels. Pixels 1006 are uncured pixels and pixels 1008 are cured pixels. As shown, the edge of pattern 1002 includes areas of varying size, including large areas such as area 1012 and area 1014, that are between cured pixels 1008 and the curvature 1010 of pattern 1002. Ideally, a process cures the entire area within curvature 1010. As shown in FIG. 10C, array 1020 shows the layout pattern 1002 shifted to a best fit. That is, this shift mitigates the uncured area inside the curvature 1010. Pixels 1026 are uncured pixels and pixels 1028 are cured pixels. However, there remains significant uncured area inside of curvature 1010 in array 1020.

Figure 10D:
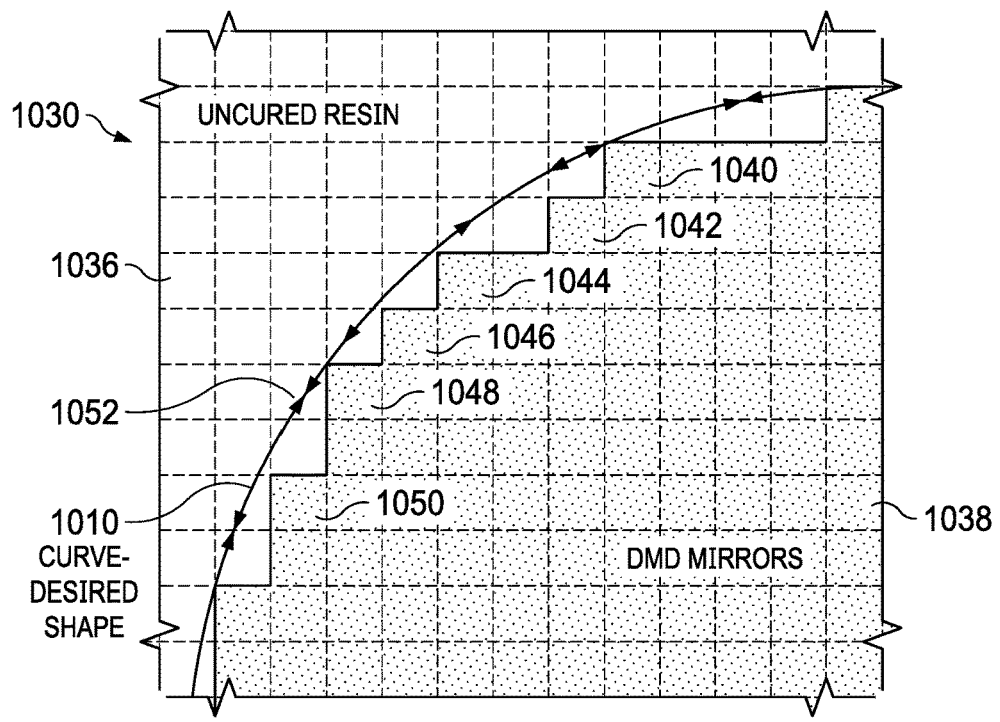
Figure 10E:
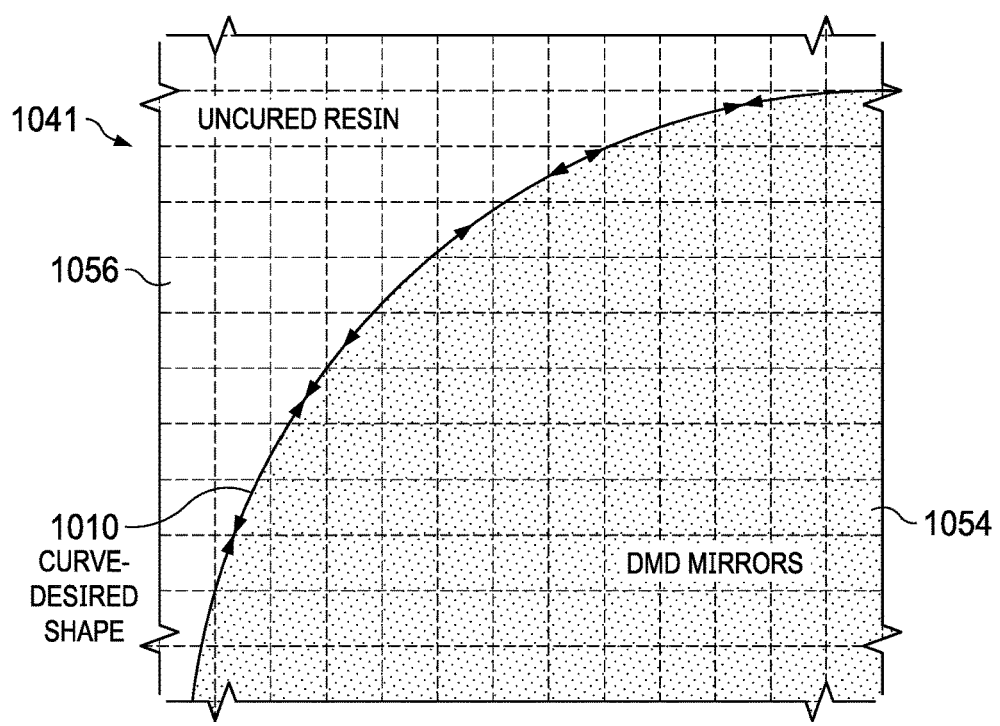

As shown in FIG. 10D, array 1030 is an array like array 1020. Pixels 1036 are uncured pixels and pixels 1038 are cured pixels. As noted above regarding array 1020, curing the whole pixels within curvature 1010 leaves a significant area of uncured pixels between cured pixels 1038 and the curvature 1010 of pattern 1002. To address these uncured pixels, this example selects the cured pixels nearest curvature 1010 for pixel shifting. In the example of array 1030, pixel 1040, pixel 1042, pixel 1044, pixel 1046, pixel 1048 and pixel 1050 shift. A pixel shifter shifts each of the selected pixels, singularly or in various combinations, so that the corner of these pixels touch curvature 1010. An analog pixel shift (further explained hereinbelow) of the pixel position of the spatial light modulator, as indicated by bi-directional arrows 1052. This example applies an illumination strategy during or between shifts of the selected pixels such that the total illumination intensity of the uncured area between curvature 1010 and cured pixels 1038 is greater than the curing threshold 404 (FIG. 4). As shown in FIG. 10E, array 1041 shows that the result is curing of the entire area 1054 under curvature 1010, while the area 1056 outside of curvature 1010 is uncured. Thus, the curing matches the desired shape. The application of this example process is not limited to any geometric shape or group of shapes.

Figure 11:
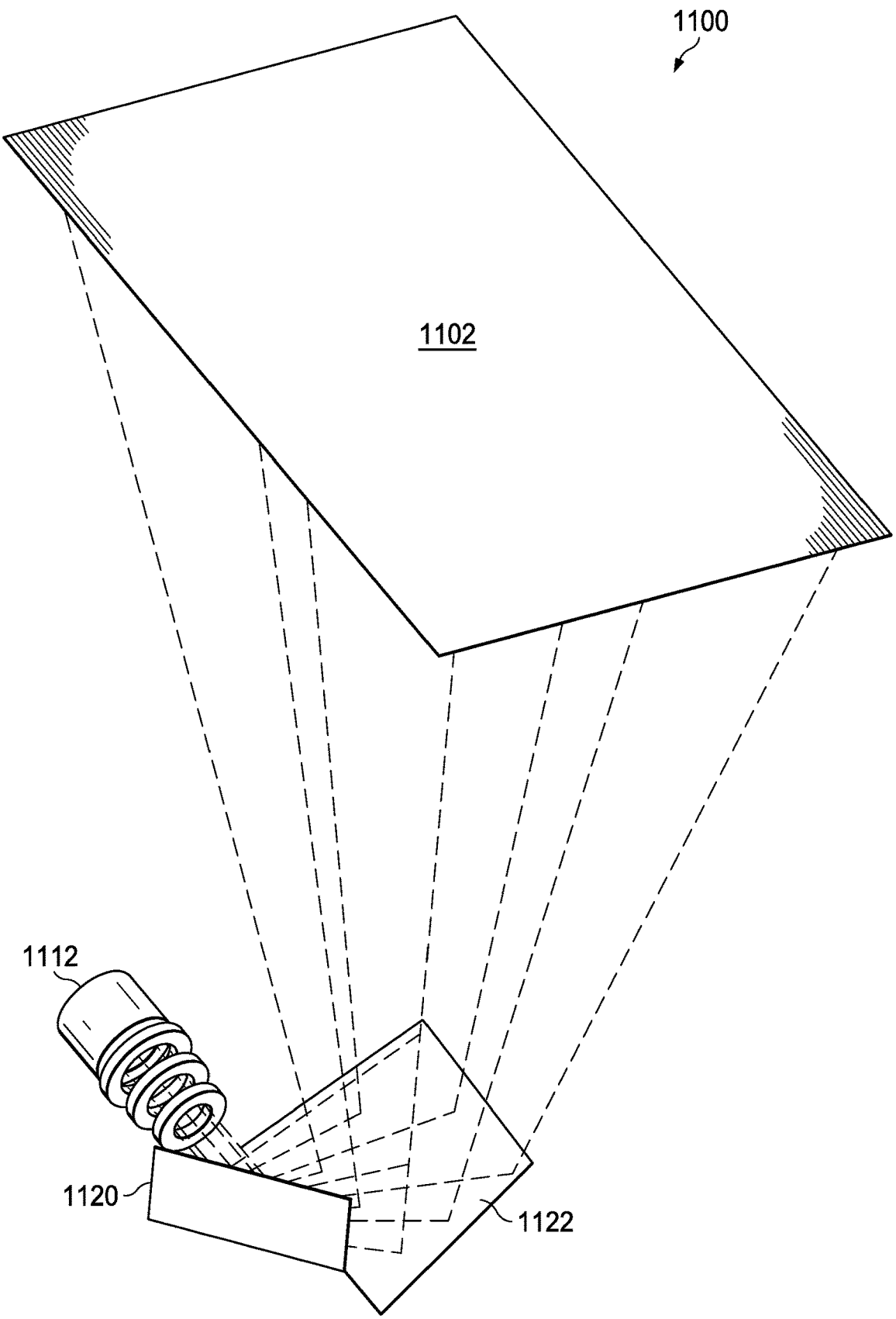
FIG. 11 is a diagram of an example arrangement of an optical engine within a three-dimensional printer.

FIG. 11 is a diagram on an example arrangement 1100 of an optical engine within a three-dimensional printer. Optical engine 1112 is like optical engine 112 (FIG. 1). In the example of FIG. 11, mirror 1120 and mirror 1122 direct the light output by optical engine 1112 to a target 1102 in a vat like vat 102 (FIG. 1).

Figure 12:
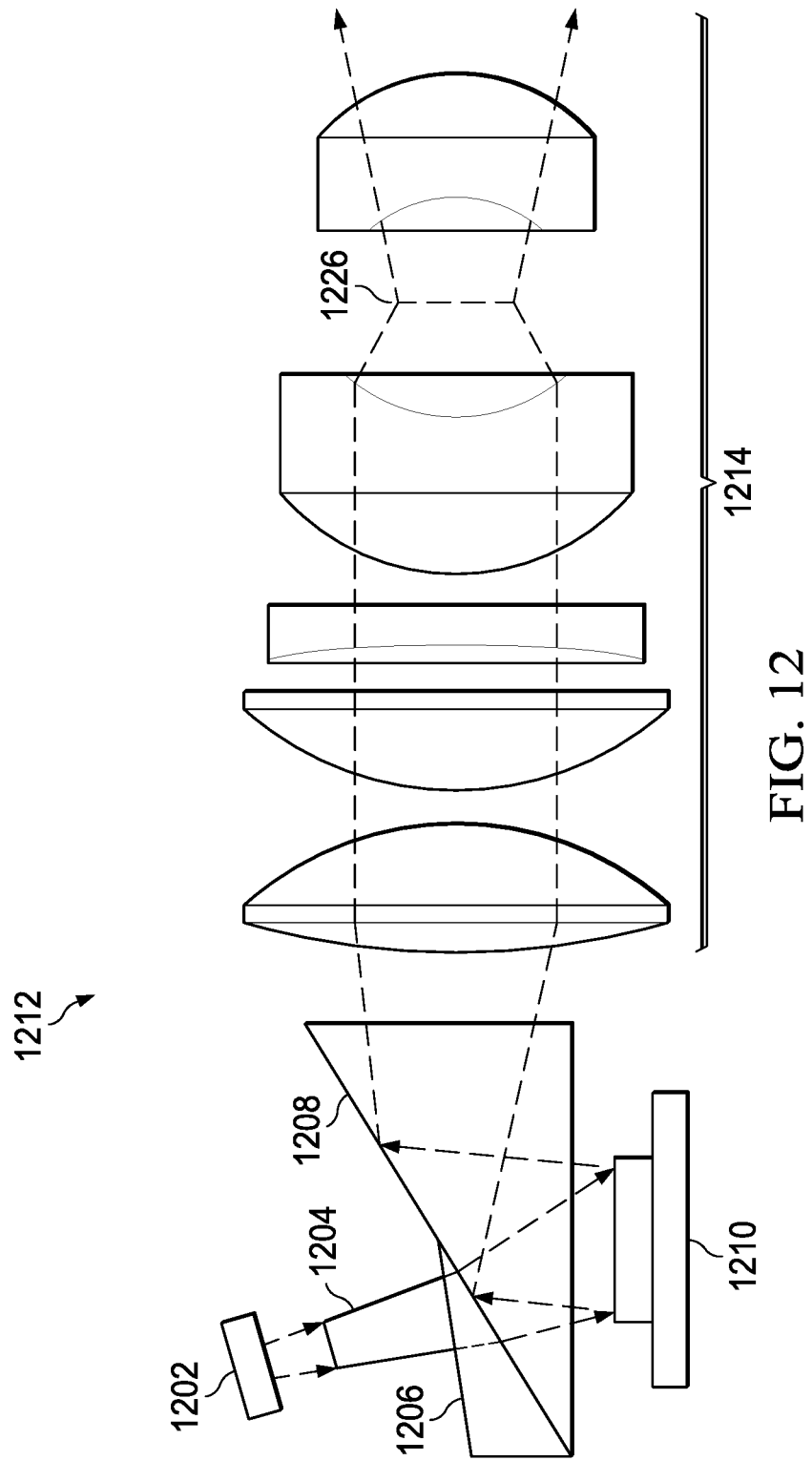
FIG. 12 is a diagram of an example optical engine.

FIG. 12 is a diagram of an example optical engine 1212. Optical engine 1212 is like optical engine 212 of FIG. 2. Light source 1202 illuminates spatial light modulator 1210 through light tunnel 1204, prism 1206, and prism 1208. The modulated light reflects from prism 1208, through projection optics 1214 to a target. In examples, mirrors like mirror 1120 and mirror 1122 (FIG. 11) direct the output of projection optics 1214. In examples, an actuator or actuators move elements of optical engine 1212 to provide a pixel shift as described hereinabove. For example, an actuator or actuators (described further hereinbelow) coupled to prism 1206, prism 1208, spatial light modulator 1210, projection optics 1214, pupil 1226, mirror 1120 (FIG. 11), and/or mirror 1122 moves one or more of these elements shifting the output pixel position. The configuration of the actuator determines the direction and amount of pixel shift.

Figure 13:
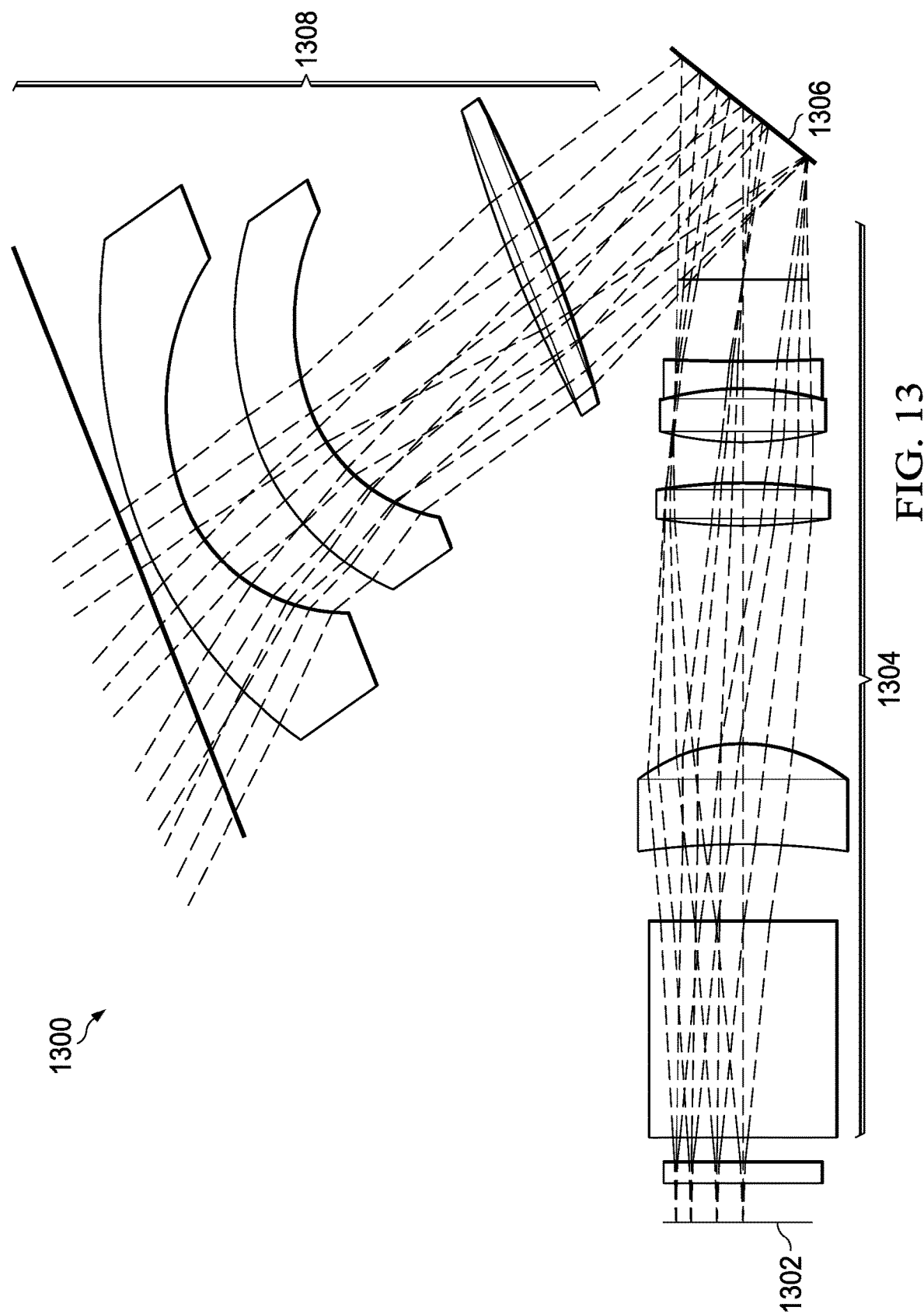
FIG. 13 is a diagram of another example optical engine.

FIG. 13 is a diagram of another example optical engine 1300. Spatial light modulator 1302 provides a modulated image to lenses 1304. Mirror 1306 is a reflective device that reflects the image from lenses 1304 to lenses 1308, which project the image to the target. In this example, mirror 1306 serves as a pixel shifting device. Mirror 1306 includes actuators (described further hereinbelow) that tilt mirror 1306 in the x and/or y direction to provide the desired pixel shift. FIG. 13 shows mirror 1306 in one position, but other examples include mirror 1306 in different places in the optical path of optical engine 1300. The selected position may be based on size of the optical engine, effect on optical quality or other design considerations.

Figure 14:
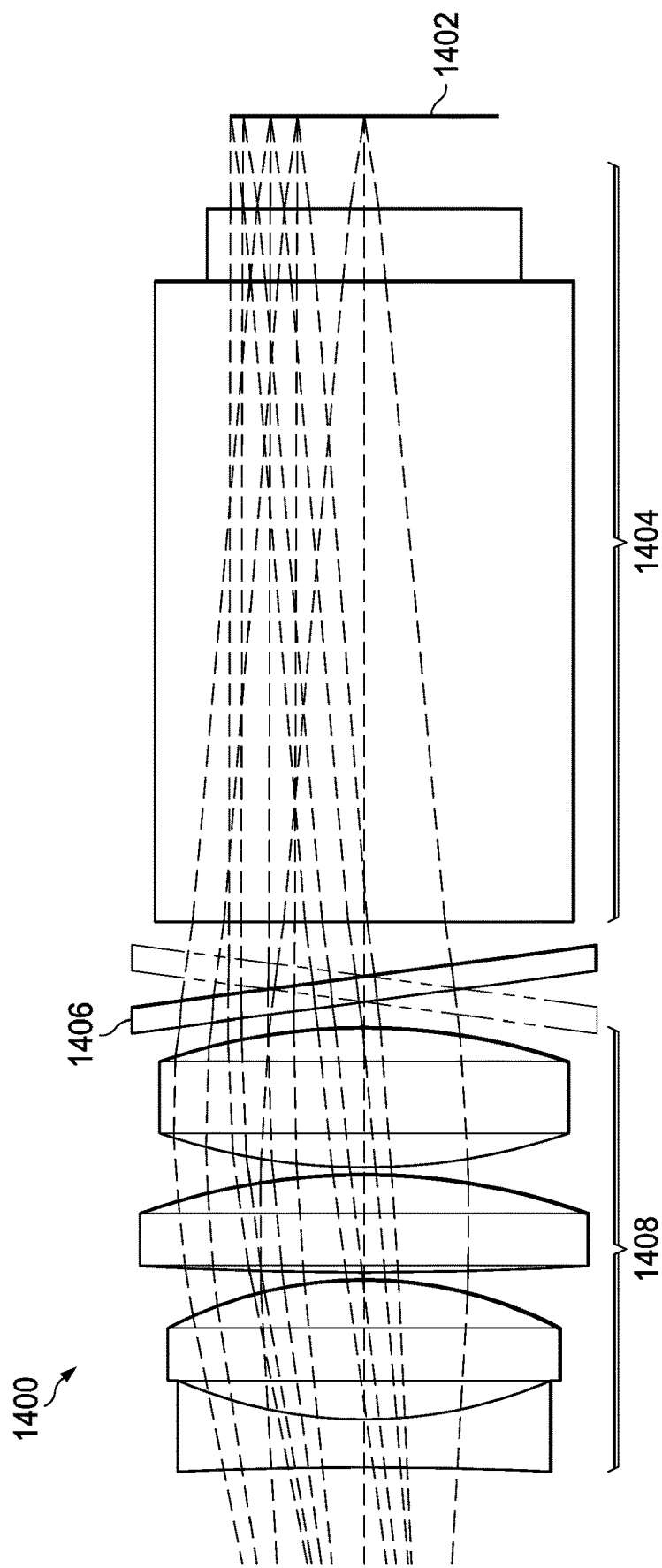
FIG. 14 is a diagram of another example optical engine.

FIG. 14 is a diagram of another example optical engine 1400. Spatial light modulator 1402 provides a modulated image to lenses 1404. The image from lenses 1404 passes through a refractive device like plate 1406 to lenses 1408 for projection. Plate 1406 includes actuators (described further hereinbelow) that tilt plate 1406 in the x and/or y direction to provide the desired pixel shift. FIG. 14 shows plate 1406 in one position, but other examples include plate 1406 in different places in the optical path of optical engine 1400. The selected position may be based on size of the optical engine, effect on optical quality or other design considerations.

Figure 15A:
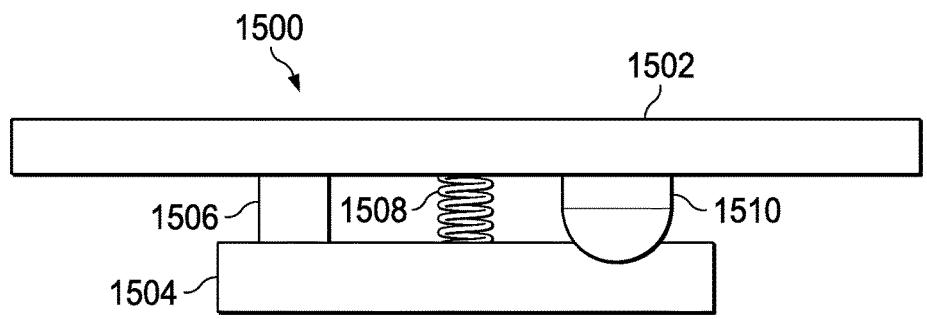
FIGS. 15A-15B (collectively "FIG. 15") are diagrams of a mirror/actuator combination.
Figure 15B:
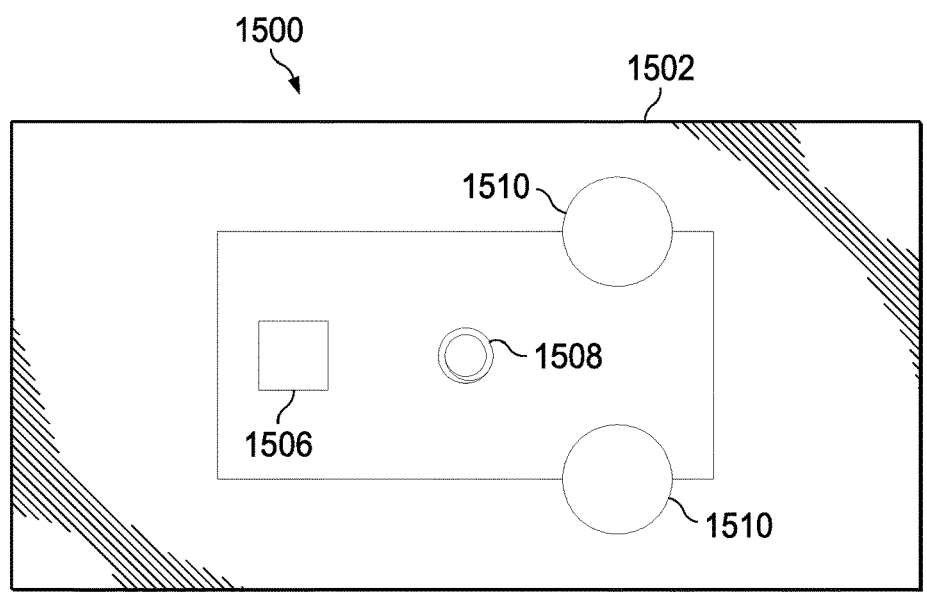

FIGS. 15A and 15B (collectively "FIG. 15") are diagrams of a mirror/actuator combination 1500. FIG. 15A is a side view and FIG. 15B is a top view through the mirror surface. The terms "side" and "top" are used herein to describe the relationship between the views and do not signify any other physical relationship. Piezo electric element 1506, spring 1508, and pivots 1510 position mirror 1502 above base 1504. Selecting a voltage applied to piezo electric element 1506 selects the tilt of mirror 1502 relative to base 1504. Changing the tilt of a mirror, like mirror 1120 (FIG. 11), mirror 1122 (FIG. 11) or mirror 1306 (FIG. 13), changes the pixel position. Using more than one mirror/actuator combination 1500 or adding another piezo electric/pivot combination to mirror/actuator combination 1500 allows for selecting a pixel shift in any direction. The use of a piezo electric elements allows for a precise pixel shift, either by increments or in an analog manner because of the linear relationship of piezo electric size change to applied voltage. A similar mechanism can be used with a plate, such as plate 1406 (FIG. 14) but on an edge of the plate to avoid impeding light through the plate. In addition, a similar mechanism can apply a shift by moving any of the components of FIG. 12.

Figure 16A:
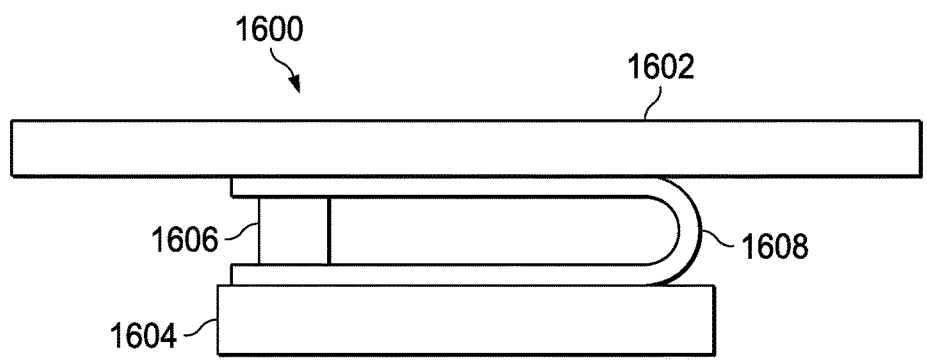
FIGS. 16A-16B (collectively "FIG. 16") are diagrams of another mirror/actuator combination.
Figure 16B:
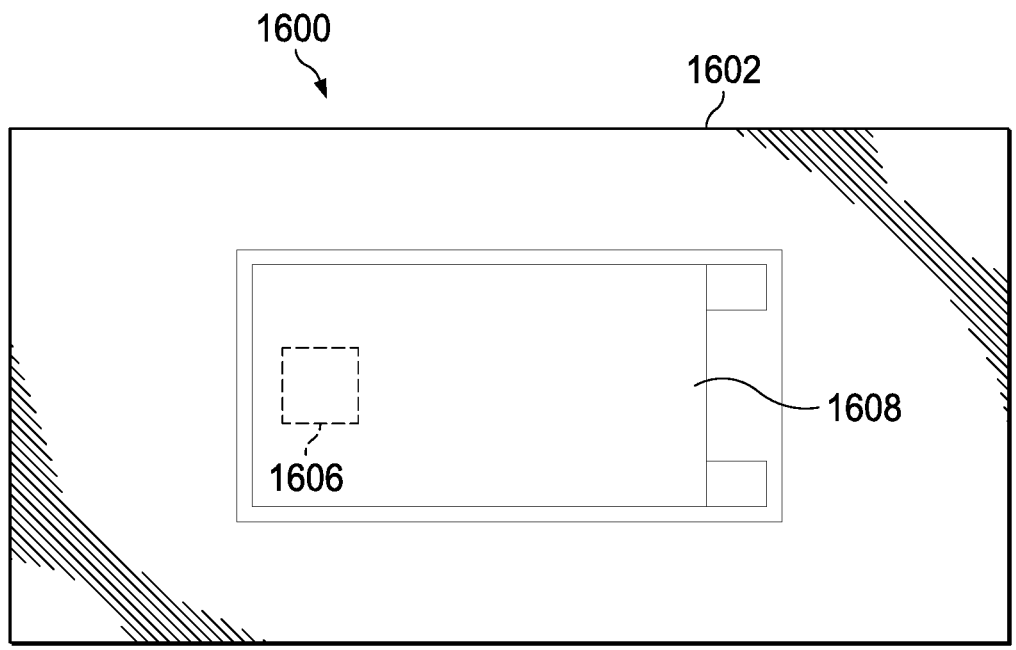

FIGS. 16A and 16B (collectively "FIG. 16") are diagrams of another mirror/actuator combination 1600. FIG. 16A is a side view and FIG. 16B is a top view through the mirror surface. The terms "side" and "top" are used herein to describe the relationship between the views and do not signify any other physical relationship. Piezo electric element 1606 and spring 1608 position mirror 1602 above base 1604. Selecting a voltage applied to piezo electric element 1606 selects the tilt of mirror 1602 relative to base 1604. Changing the tilt of a mirror, like mirror 1120 (FIG. 11), mirror 1122 (FIG. 11) or mirror 1306 (FIG. 13), changes the pixel position. Using more than one mirror/actuator combination 1600 or adding another piezo electric/spring combination to mirror/actuator combination 1600 allows for selecting a pixel shift in any direction. The use of a piezo electric elements allows for a precise pixel shift, either by increments or in an analog manner because of the linear relationship of piezo electric size change to applied voltage. A similar mechanism can be used with a plate, such as plate 1406 (FIG. 14) but on an edge of the plate to avoid impeding light through the plate. In addition, a similar mechanism can apply a shift by moving any of the components of FIG. 12.

Figure 17A:
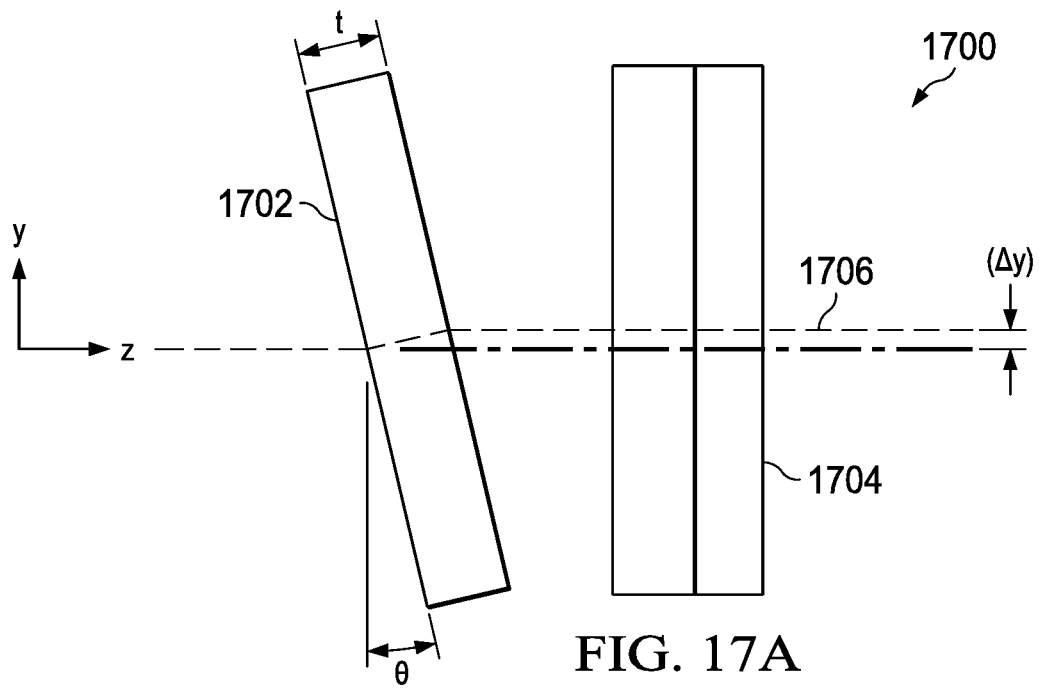
FIGS. 17A-17C (collectively "FIG. 17") are diagrams of an example pixel shifter using two flat plates.
Figure 17B:
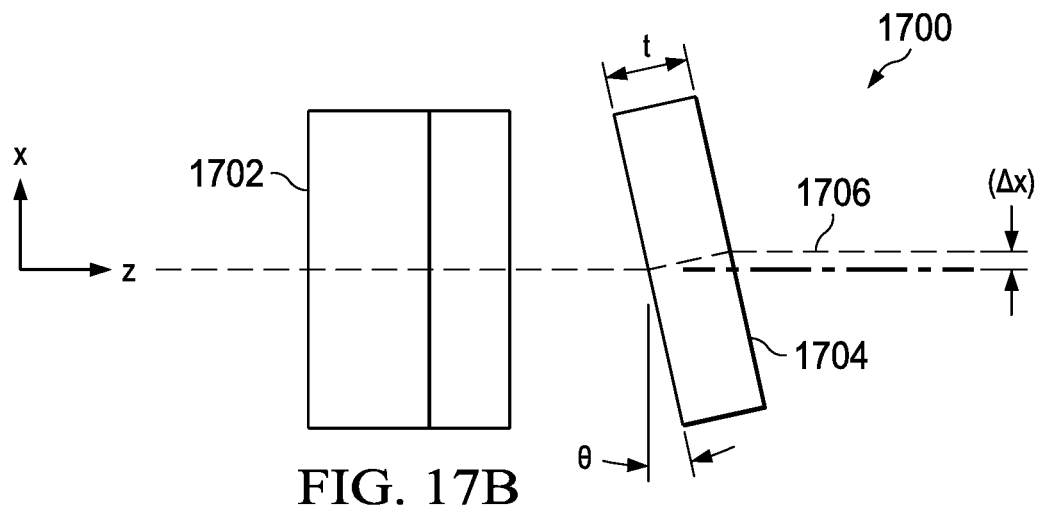
Figure 17C:
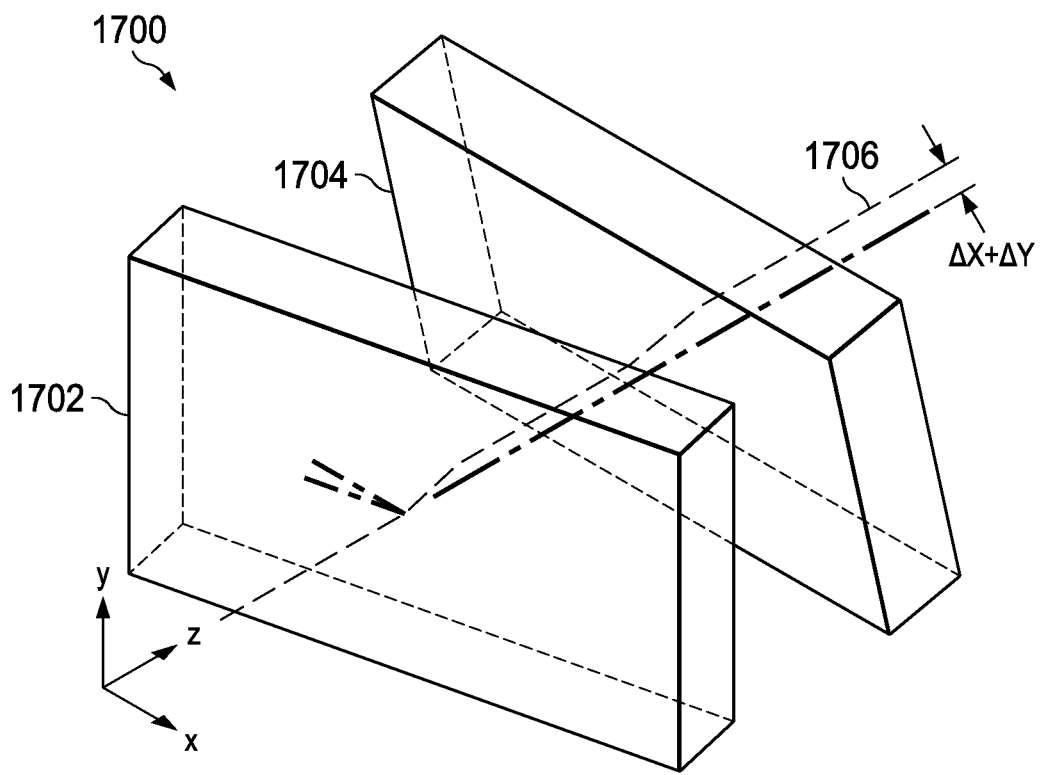

FIGS. 17A-17C (collectively "FIG. 17") are diagrams of an example pixel shifter 1700 using two flat plates. As shown in FIG. 17A, plate 1702 tilts on an axis that is parallel to the x-axis (i.e., into the page) as actuated by an actuator such as a piezo electric actuator. Plate 1702 has an index of refraction n that is greater than one (greater than air). The light travels on the z-axis through plate 1702. Because the light is at an angle to the surface of plate 1702 and because plate 1702 has an index of refraction different from air, the light 1706 diffracts at an angle θ at the interface between the air and the plate. Light 1706 then diffracts oppositely when exiting plate 1702. The result is a shift of light 1706 by Δy, which is determined by $$\Delta y = t \cdot \frac{n_1}{n_2} \sin\theta \qquad (1)$$

where t is the thickness of plate 1702, $n_1$ is the index of refraction of air (which is 1), and $n_2$ is the index of refraction of plate 1702. Similarly, plate 1704 tilts on an axis parallel to the y-axis as shown in FIG. 17B as actuated by an actuator such as a piezo electric actuator. This creates a pixel shift in the x-direction Δx in the same manner that plate 1702 creates a pixel shift in the y-direction. The combination of shifts by plate 1702 and 1704 enables pixel shifting in any direction in the x-y plane. FIG. 17C shows plate 1702 and plate 1704 in a perspective view.

Figure 18A:
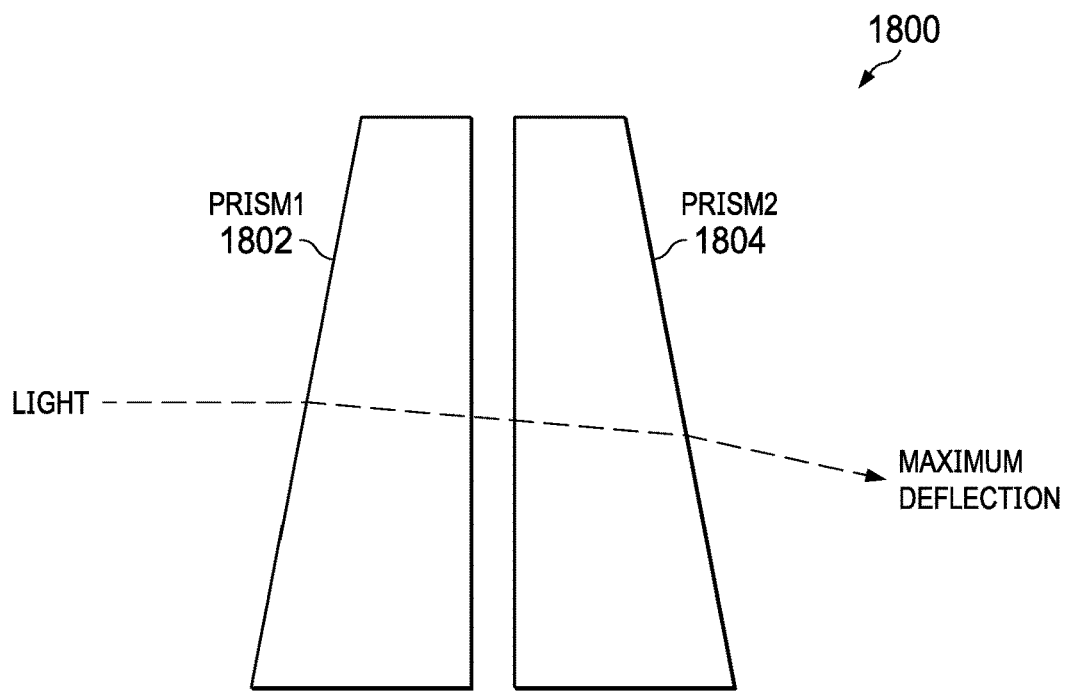
FIG. 18A-18C (collectively "FIG. 18") are views of an example beam direction device for pixel shifting.
Figure 18B:
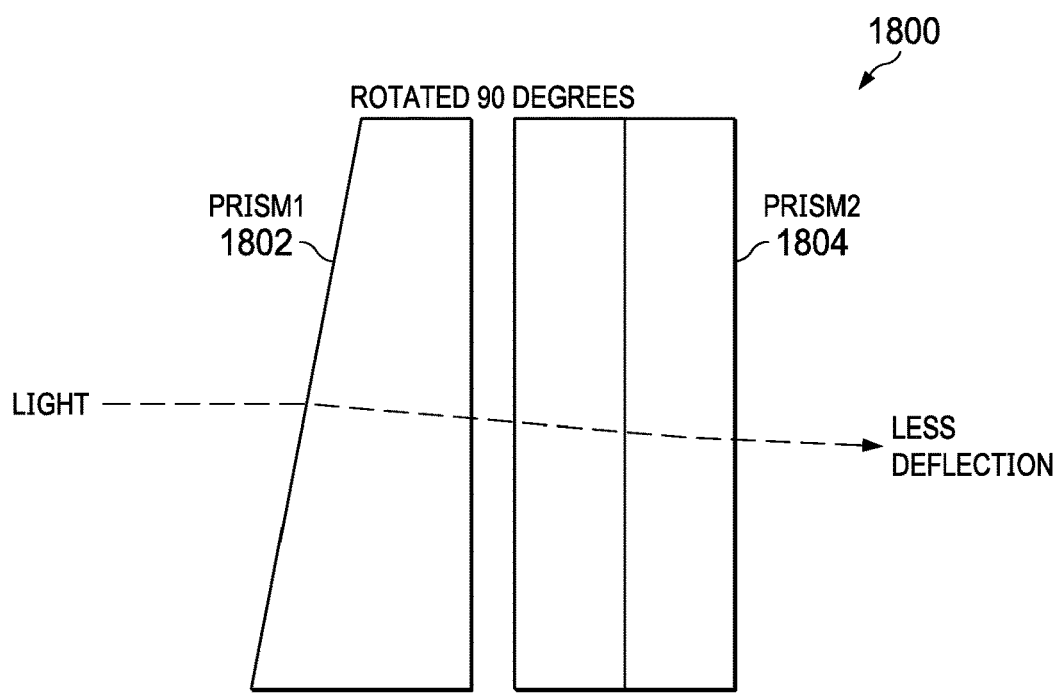
Figure 18C:
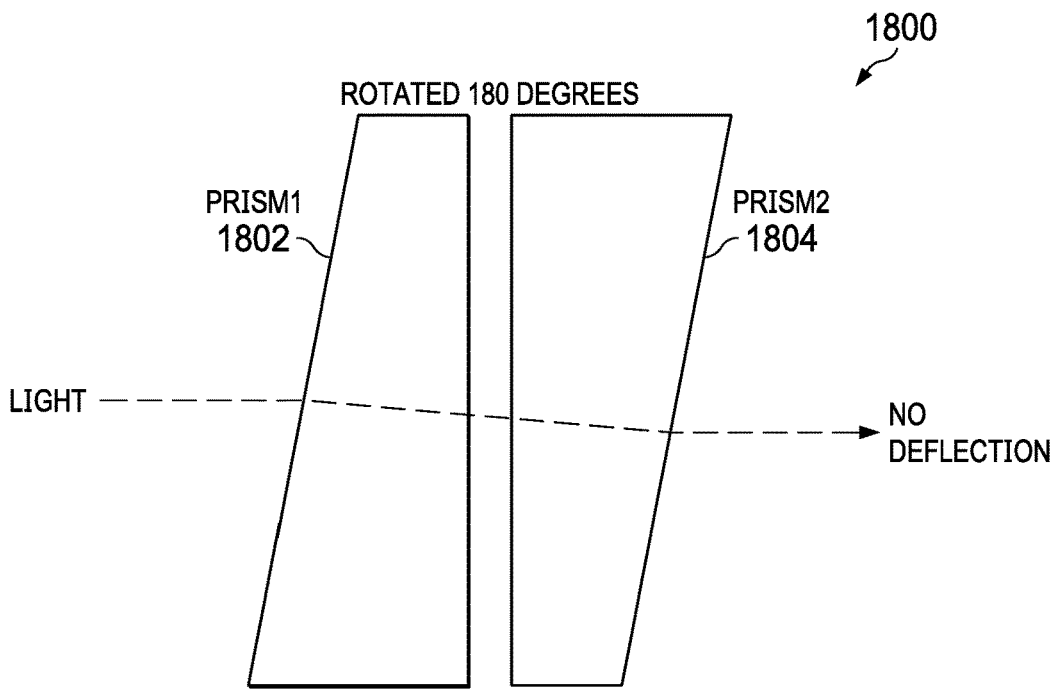

FIGS. 18A-18C (collectively "FIG. 18") are views of an example beam direction device for pixel shifting. As shown in FIG. 18A, Risley prism 1800 includes two wedge prisms: prism 1802 and prism 1804. Rotating prism 1804 relative to prism 1802 changes the direction of the light through Risley prism 1800. In FIG. 18A, the wedged faces of prism 1802 and prism 1804 slope away from each other from top to bottom. This configuration provides a maximum deflection downward that Risley prism 1800 can provide. In FIG. 18B, prism 1804 turns ninety degrees from prism 1804 in FIG. 18A with the thicker portion of prism 1804 away from the page. This configuration provides less deflection. In FIG. 18C, the wedged faces of prism 1802 and prism 1804 are parallel. This configuration provides the minimal deflection. Thus, the deflection properties of a Risley prism like Risley prism 1800 can accomplish pixel shifting.

Figure 19:
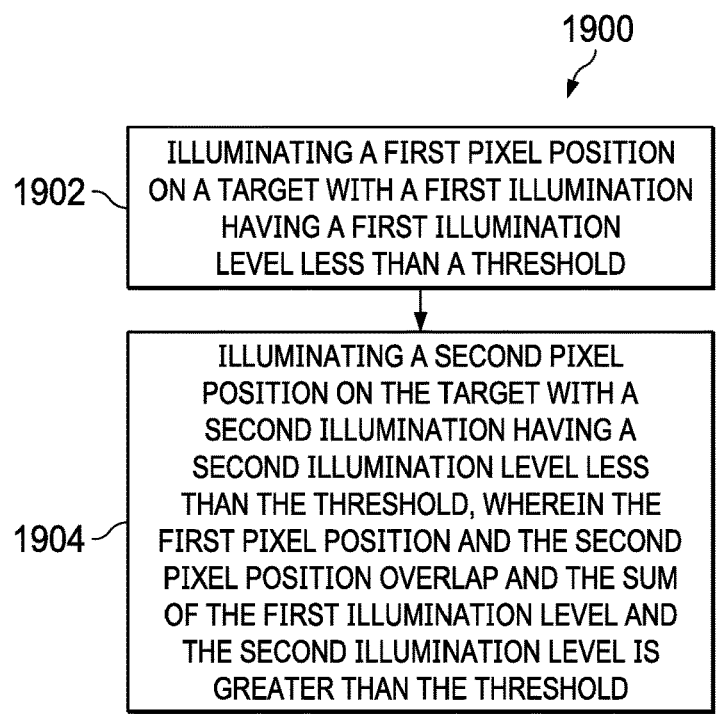
FIG. 19 is a process flow diagram of an example process.

FIG. 19 is a process flow diagram of an example process 1900. Step 1902 is illuminating a first pixel position on a target with a first illumination having a first illumination level less than a threshold. The first pixel position is like pixel 304 (FIG. 3). The target is like target 218 (FIG. 2) or photo-polymerizing resin 108 (FIG. 1). The first illumination level is like illumination level 412 (FIG. 4). The threshold is like curing threshold 404 (FIG. 4). Step 1904 is illuminating a second pixel position on the target with a second illumination having a second illumination level less than the threshold, wherein the first pixel position and the second pixel position overlap and the sum of the first illumination level and the second illumination level is greater than the threshold. The second pixel position is like pixel 306 (FIG. 3). The second illumination level is light illumination level 412 (FIG. 4). The overlap is like overlap 308 (FIG. 3).

Modifications are possible in the described examples, and other examples are possible, within the scope of the claims.

What is claimed is:

1. A device, comprising:
   a light source configured to provide first light and second light;
   a spatial light modulator optically coupled to the light source, the spatial light modulator configured to modulate the first light to produce first modulated light and to modulate the second light to produce second modulated light;
   an optical assembly comprising a first component, the optical assembly configured to direct the first light and the second light towards the spatial light modulator;
   projection optics comprising a second component, the projection optics optically coupled to the spatial light modulator and adapted to be optically coupled to a target having first and second pixel regions that partially overlap, the projection optics configured to project the first modulated light onto the first pixel region and to project the second modulated light onto the second pixel region; and
   a pixel shifter physically coupled to the first component, to the second component, or to the spatial light modulator, the pixel shifter configured to move the first component, the second component, or the spatial light modulator between:
   a first position while the spatial light modulator outputs the first modulated light; and
   a second position while the spatial light modulator outputs the second modulated light.

2. The device of claim 1, wherein the first light has a first intensity, and the second light has a second intensity equal to the first intensity.

3. The device of claim 1, wherein the light source is a light emitting diode.

4. The device of claim 1, wherein the spatial light modulator is a digital micromirror device.

5. The device of claim 1, wherein the target is a resin, the first light has a first intensity below a curing threshold of the resin, the second light has a second intensity below the curing threshold, and a sum of the first and second intensities exceeds the curing threshold.

6. The device of claim 5, wherein the resin is a photo-polymerizing resin.

7. The device of claim 1, wherein the pixel shifter is coupled to the spatial light modulator and is configured to move the spatial light modulator between the first and second positions, so the spatial light modulator has the first position when the spatial light modulator outputs the first modulated light, and the spatial light modulator has the second position when the spatial light modulator outputs the second modulated light.

8. The device of claim 1, wherein the pixel shifter is coupled to the second component and is configured to move the second component between the first and second positions, so the second component has the first position when the spatial light modulator outputs the first modulated light, and the second component has the second position when the spatial light modulator outputs the second modulated light.

9. The device of claim 8, wherein the second component is a refractive device.

10. The device of claim 8, wherein the second component is a reflective device.

11. A three-dimensional printer comprising:
    a resin vat having a transparent bottom;
    a lift plate insertable within the resin vat;
    a light source configured to provide first light and second light;
    a spatial light modulator optically coupled to the light source, the spatial light modulator configured to modulate the first light to produce first modulated light and to modulate the second light to produce second modulated light;
    an optical assembly comprising a first component, the optical assembly configured to direct the first light and the second light towards the spatial light modulator;
    projection optics comprising a second component, the projection optics optically coupled to the spatial light modulator and adapted to be optically coupled through the transparent bottom to a resin on the lift plate, the resin having first and second pixel regions that partially overlap, the projection optics configured to project the first modulated light onto the first pixel region and to project the second modulated light onto the second pixel region; and
    a pixel shifter physically coupled to the first component, to the second component, or to the spatial light modulator, the pixel shifter configured to move the first component, the second component, or the spatial light modulator between:
    a first position when the spatial light modulator outputs the first modulated light; and
    a second position when the spatial light modulator outputs the second modulated light.

12. The three-dimensional printer of claim 11, wherein the first light has a first intensity, and the second light has a second intensity equal to the first intensity.

13. The three-dimensional printer of claim 11, wherein the spatial light modulator is a digital micromirror device.

14. The three-dimensional printer of claim 11, wherein the pixel shifter is coupled to the spatial light modulator and is configured to move the spatial light modulator between the first and second positions, so the spatial light modulator has the first position when the spatial light modulator outputs the first modulated light, and the spatial light modulator has the second position when the spatial light modulator outputs the second modulated light.

15. The three-dimensional printer of claim 11, wherein the pixel shifter is coupled to the second component and is configured to move the second component between the first and second positions, so the second component has the first position when the spatial light modulator outputs the first modulated light, and the second component has the second position when the spatial light modulator outputs the second modulated light.

16. The three-dimensional printer of claim 15, wherein the second component is a refractive device.

17. The three-dimensional printer of claim 15, wherein the second component is a reflective device.

18. The three-dimensional printer of claim 11, wherein the first light has a first intensity below a curing threshold of the resin, the second light has a second intensity below the curing threshold, and a sum of the first and second intensities exceeds the curing threshold.

19. The three-dimensional printer of claim 18, wherein the resin is a photo-polymerizing resin.

20. A system comprising:
a light source configured to provide first light and second light;
a spatial light modulator configured to:
modulate the first light to produce first modulated light; and
modulate the second light to produce second modulated light;
an optical assembly comprising a first component, the optical assembly configured to direct the first light and the second light towards the spatial light modulator;
projection optics comprising a second component, the projection optics configured to:
project the first modulated light onto a first pixel region; and
project the second modulated light onto a second pixel region; and
a pixel shifter physically coupled to the first component, to the second component, or to the spatial light modulator, the pixel shifter configured to move the first component, the second component, or the spatial light modulator between:
a first position while the spatial light modulator outputs the first modulated light; and
a second position while the spatial light modulator outputs the second modulated light.

21. The system of claim 20, wherein the pixel shifter is physically coupled to the first component, and the first component comprises a prism.

22. The system of claim 20, wherein the pixel shifter is physically coupled to the second component, and the second component comprises a prism.

23. The system of claim 20, wherein the pixel shifter is physically coupled to the second component, and the second component comprises a pupil.

24. The system of claim 20, wherein the pixel shifter is physically coupled to the second component, and the second component comprises a plate.

25. The system of claim 20, wherein the pixel shifter is physically coupled to the second component, and the second component comprise a prism.

26. The system of claim 20, wherein the pixel shifter is physically coupled to the spatial light modulator.

* * * * *